US 6,541,471 B1

(12) United States Patent
Lavielle et al.

(10) Patent No.: US 6,541,471 B1
(45) Date of Patent: Apr. 1, 2003

(54) BENZENESULPHONAMIDE COMPOUNDS

(75) Inventors: Gilbert Lavielle, La Celle Saint Cloud (FR); Thierry Dubuffet, Bolbec (FR); Bernard Cimetiere, Paris (FR); Tony Verbeuren, Vernouillet (FR); Serge Simonet, Conflans Sainte Honorine (FR); Christine Vayssettes-Courchay, Igny (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/195,018

(22) Filed: Jul. 12, 2002

(30) Foreign Application Priority Data

Jul. 13, 2001 (FR) .............................. 01 09339

(51) Int. Cl.$^7$ ................. A61K 31/5375; A61P 7/02; C07D 295/153
(52) U.S. Cl. ............... 514/239.2; 544/159; 544/368; 544/399; 546/198; 548/575; 562/430
(58) Field of Search ................. 544/159; 548/575; 562/430; 514/239.2

(56) References Cited

U.S. PATENT DOCUMENTS 5,597,848 A * 1/1997 Ito et al. ............... 562/430

* cited by examiner

*Primary Examiner*—Robert W. Ramsuer
(74) *Attorney, Agent, or Firm*—The Firm of Hueschen and Sage

(57) ABSTRACT

A compound of formula (I):

$$G-(CH_2)_r-O-\text{Ar}-(O)_m-(CH_2)_n-\text{Ar}'(R^3)-(CH_2)_q- \; ; \; (CH_2)_p-CO-R_a \; ; \; -NH-SO_2-\text{Ar}''(R_b,R_c)$$

(I)

wherein:
G represents a group such as:

$$-N\begin{matrix}R^1\\R^2\end{matrix}$$

wherein $R^1$ and $R^2$ independently represent a hydrogen atom or an alkyl, cycloalkyl, aryl, arylalkyl, cycloalkyl, cycloalkylalkyl, heteroaryl or heteroarylalkyl group, or, $R^1$ and $R^2$ together with the nitrogen atom form a heterocycloalkyl group, $R^3$ represents a hydrogen atom or an alkyl or optionally substituted phenyl group, $R_a$ represents a hydroxy group, a linear or branched $(C_1-C_6)$alkoxy group or an amino group, $R_b$ and $R_c$, which may be identical or different, each represents a hydrogen atom, a halogen atom, an alkyl group, an alkoxy group, a hydroxy group or a trihaloalkyl group, m is an integer of from 0 to 1 inclusive,
n and q are integers of from 0 to 6 inclusive,
p and r are integers of from 1 to 6 inclusive, its enantiomers and diastereoisomers, and addition salts thereof with a pharmaceutically acceptable acid or base; and medicinal products containing the same which are useful as a $TXA_2$ receptor antagonist and a $5-HT_2$ receptor antagonist.

19 Claims, No Drawings

BENZENESULPHONAMIDE COMPOUNDS

SUMMARY OF THE INVENTION

The present invention relates to new benzenesulphonamide compounds, and to pharmaceutical compositions containing them.

The compounds of the present invention have a novel structure giving them a $TXA_2$ receptor antagonist and $5HT_2$ serotoninergic receptor antagonist character.

DESCRIPTION OF THE PRIOR ART

Compounds having a benzenesulphonamide chain have been described in Application EP 864 561 in relation to their NO-yielding character and their thromboxane $A_2$ ($TXA_2$) receptor antagonist character, as well as in Applications EP 648 741 or WO 9406761 solely in relation to their $TXA_2$ receptor antagonist properties.

BACKGROUND OF THE INVENTION

Platelet aggregation and vasospasms play an essential role in the aetiology and development of atherothrombotic cardiovascular diseases. $TXA_2$, an arachidonic acid metabolite, and serotonin (5HT), a neurotransmitter, are both powerful vasoconstrictor agents, and are able to induce or reinforce platelet activation, resulting in the aggregation thereof The vasoconstrictor and pro-aggregation actions of $TXA_2$ are effected through the intermediary of membrane receptors called TP receptors (Medicinal Research Reviews, 1991, 11 5, p. 503) while those of serotonin are effected through the intermediary of $5HT_1$ or $5HT_2$ receptors (T.I.P.S., 1991, 121, p. 223). Research strategies pursued with the aim of finding agents that block the production and/or activation of $TXA_2$ have led to the development of selective TP receptor antagonists, of $TXA_2$-synthase inhibitors, or of mixed agents that exhibit both properties (Medicinal Research Reviews, ibid., T.I.P.S., 1991, 121, 158). Like $TXA_2$, serotonin acts by stimulating platelets and vascular constriction and its activity is found to be increased in atherothrombotic diseases.

The idea of compounds that oppose both the process that causes thromboxane to become active and the process that causes serotonin to become active is extremely useful for the clinician. Such products have the advantage of offering more complete protection both against the activation of platelets and against vasospasms. It will thus be possible for such products to be used in the treatment of pathologies associated with increased activity of $TXA_2$ and 5-HT especially in the treatment of atherothrombotic cardiovascular diseases, such as myocardial infarction, angina pectoris, cerebral vascular accidents, Raynaud's disease, and also asthma and bronchospasms, as well as migraine and venous diseases.

DETAILED DESCRIPTION OF THE INVENTION

The present invention relates to the compounds of formula (I):

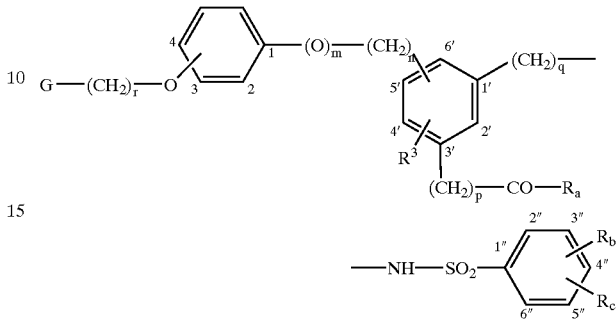

(I)

wherein:

G represents a group such as:

wherein $R^1$ and $R^2$ independently represent a hydrogen atom, or an alkyl, cycloalkyl, optionally substituted aryl, optionally substituted arylalkyl, cycloalkyl, cycloalkylalkyl, optionally substituted heteroaryl or optionally substituted heteroarylalkyl group, or
$R^1$ and $R^2$ together with the nitrogen atom form a heterocycloalkyl group of formula

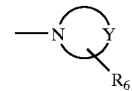

having from 5 to 7 ring members, wherein Y represents a nitrogen atom, an oxygen atom or a $CH_2$ group and $R_6$ represents a hydrogen atom or an alkyl, cycloalkyl, cycloalkylalkyl, optionally substituted aryl, optionally substituted arylalkyl, optionally substituted arylcarbonyl, optionally substituted arylcarbonylalkyl, optionally substituted diarylalkyl, optionally substituted diarylalkenyl, optionally substituted heteroaryl, optionally substituted heteroarylalkyl, optionally substituted heteroarylcarbonyl or optionally substituted heteroarylcarbonylalkyl group, $R^3$ represents a hydrogen atom or an alkyl or optionally substituted phenyl group, $R_a$ represents a hydroxy, alkoxy, optionally substituted aryloxy, optionally substituted arylalkyloxy, amino, alkylamino, dialkylamino, optionally substituted arylamino or optionally substituted arylalkylamino group, $R_b$ and $R_c$, which may be identical or different, each represents a hydrogen atom, a halogen atom, an alkyl group, an alkoxy group, a hydroxy group or a trihaloalkyl group, m is an integer of from 0 to 1 inclusive, n and q are identical or different integers of from 0 to 6 inclusive, p and r are identical or different integers of from 1 to 6 inclusive, to their enantiomers and diastereoisomers, and also to addition salts thereof with a pharmaceutically acceptable acid or base, wherein:

the term "alkyl" denotes a linear or branched chain having from 1 to 6 carbon atoms, the term "alkoxy" denotes a linear or branched alkyl-oxy group having from 1 to 6 carbon atoms, the term "trihaloalkyl" denotes a carbon chain having from 1 to 3 carbon atoms and from 1 to 3 identical or different halogen atoms, the term "alkenyl" denotes a chain having from 2 to 6 carbon atoms and containing from 1 to 3 double bonds, the term "cycloalkyl" denotes a saturated cyclic group having from 3 to 8 carbon atoms, the term "aryl" denotes a phenyl or naphthyl group, the term "heteroaryl" denotes an aromatic monocyclic group, or a bicyclic group in which at least one of the rings is aromatic, having from 5 to 11 ring members and from 1 to 5 hetero atoms selected from nitrogen, oxygen and sulphur, the terms "diarylalkyl" and "diarylalkenyl" denote, respectively, alkyl and alkenyl groups as defined hereinbefore, substituted by two identical or different aryl groups as defined hereinbefore, the term "substituted" relating to phenyl, aryl, arylalkyl, arylcarbonyl, arylcarbonylalkyl, diarylalkyl, diarylalkenyl, heteroaryl, heteroarylalkyl, heteroarylcarbonyl, heteroarylcarbonylalkyl, arylamino and arylalkylamino denotes that the groups in question are substituted in the aromatic moiety by one or two identical or different substituents selected from halogen atoms and alkyl groups, alkoxy groups, hydroxy groups, cyano groups, nitro groups, amino groups (optionally substituted by one or two alkyl groups) and groups $C(O)R_d$, $R_d$ representing a group selected from hydroxy, alkoxy and amino, wherein the heteroaryl and heteroarylalkyl groups may also be substituted by an oxo group in the non-aromatic moiety of the heteroaryl.

Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric acid, etc.

Amongst the pharmaceutically acceptable bases there may be mentioned, without implying any limitation, sodium hydroxide, potassium hydroxide, triethylamine, tert-butylamine etc.

Preferred compounds of formula (I) are those wherein, taken together or separately, the value of p is 2, the value of q is 2, the substituent $R^3$ represents a hydrogen atom, the substituent $R_a$ represents a hydroxy group, the substituent $R_b$ represents a halogen atom and the substituent $R_c$ represents a hydrogen atom.

An especially advantageous embodiment of the invention relates to compounds of formula (I) wherein p and q are each 2, $R_a$ represents a hydroxy group, $R^3$ and $R_c$ each represents a hydrogen atom, $R_b$ represents a halogen atom and G represents an amino, dialkylamino or arylalkylamino group or a heterocycloalkyl group of formula:

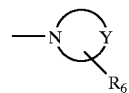

wherein Y represents a nitrogen atom, an oxygen atom or a $CH_2$ group and $R_6$ is selected from a hydrogen atom and the groups optionally substituted aryl and optionally substituted heteroaryl.

In preferred compounds of formula (I), G represents a dialkylamino group.

Other preferred compounds of formula I are those wherein G represents a substituted heterocycloalkyl group

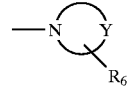

wherein:

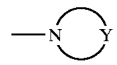

represents a group having 5 or 6 ring members, such as: pyrrolyl, morpholino, piperidyl or piperazinyl, and $R_6$ substituted on a carbon or nitrogen atom of the heterocycloalkyl represents a hydrogen atom, a phenyl substituent optionally substituted by a halogen atom, or a heteroaryl group having 9 ring members that contains one or two hetero atoms selected from nitrogen, oxygen and sulphur and is optionally substituted by a halogen atom.

Preferred compounds of formula (I) are those wherein the optionally substituted heteroaryl group represents a benzisoxazolyl group optionally substituted by a halogen atom, or a benzisothiazolyl group optionally substituted by a halogen atom.

Advantageously, the invention relates to compounds of formula (I) wherein, taken together or separately, the substituent G—$(CH_2)_r$—O— is attached to one of the two carbon atoms 2 or 4 of the phenyl group, the substituent

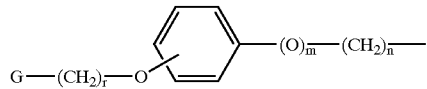

is attached to the 5' carbon atom of the phenyl group, and $R_b$ is attached to the 4" atom of the phenyl group.

Of the preferred compounds of the invention, the following may be mentioned:

3-[3-(2-{[(4-chlorophenyl)sulphonyl]amino}ethyl)-5-(2-{2-[3-(dimethylamino)-propoxy]phenyl}ethyl)phenyl] propanoic acid 3-[3-(2-{[(4-chlorophenyl)sulphonyl]amino}ethyl)-5-(2-{2-[2-(1-pyrrolidinyl)-ethoxy]phenyl}ethyl)phenyl] propanoic acid 3-[3-(2-{[(4-chlorophenyl)sulphonyl]amino}ethyl)-5-(2-{2-[2-(4-morpholinyl)-ethoxy]phenyl}ethyl)phenyl] propanoic acid.

The present invention relates also to a process for the preparation of compounds of formula (I) which is characterised in that:

1) when it is desired to obtain compounds of formula (I) wherein m=0 and n is other than 1, there is used as starting material a compound of formula (II):

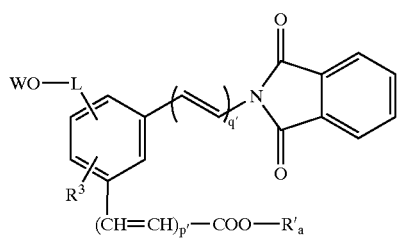

wherein $R^3$ is as defined for formula (I), $R'_a$ represents a linear or branched ($C_1$–$C_6$)alkyl group, WO-L represents a group of formula:

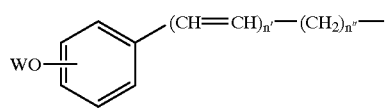

in which W represents a hydrogen atom or a benzyl group, p' and q' are integers of from 0 to 3, and n'+n"=an integer of from 0 to 3 provided that, when n' is 0, n" is 0, 2 or 3, which is catalytically reduced to yield, after debenzylation when W represents a benzyl group, a compound of formula (III):

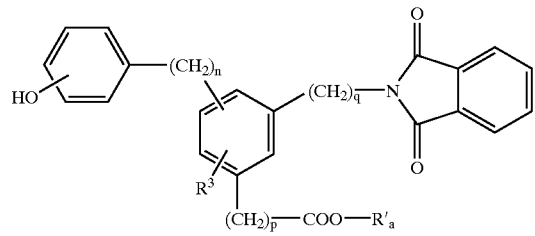

wherein $R^3$, n, p and q are as defined for formula (I) and $R'_a$ represents a linear or branched ($C_1$–$C_6$)alkyl group, which is condensed in basic medium with a halide of formula: G—(CH$_2$)$_r$—X, wherein X represents a halogen atom, to yield a compound of formula (IV):

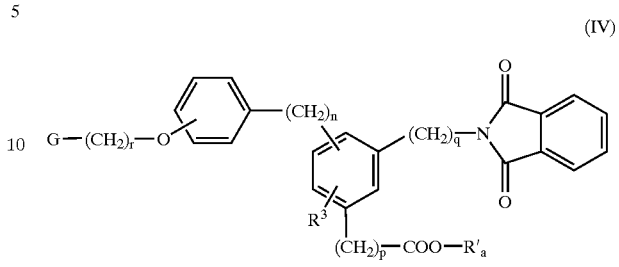

wherein G, $R^3$, n, p, q and r are as defined for formula (I) and $R'_a$ represents a linear or branched ($C_1$–$C_6$) alkyl group, which is deprotected by cleavage of the phthalimido group in the presence of hydrazine to yield the corresponding amine which, in turn, is reacted with an optionally substituted benzenesulphonyl halide of formula:

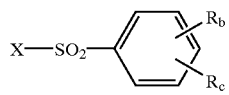

wherein $R_b$ and $R_c$ are as defined for formula (I) and X represents a halogen atom, to yield a compound of formula (I/a), a particular case of the compounds (I):

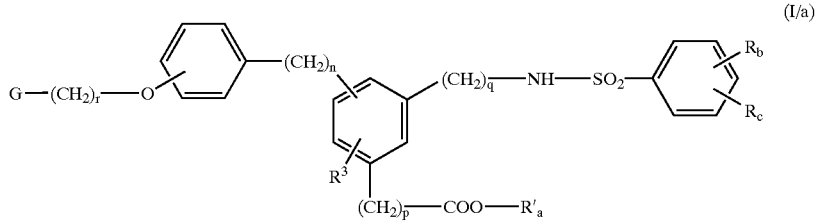

wherein G, $R_b$, $R_c$, $R^3$, r, n, p and q are as defined for formula (I) and $R'_a$ represents a linear or branched ($C_1$–$C_6$)alkyl group, 2) when it is desired to obtain compounds of formula (I) wherein m=1, or wherein m=0 and n=1, there is used as starting material a compound of formula (II/a):

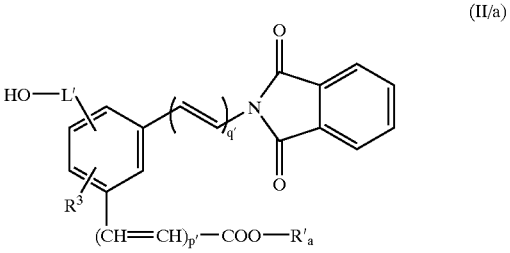

wherein $R^3$ is as defined for formula (I), $R'_a$ represents a linear or branched ($C_1$–$C_6$)alkyl group, HO-L' represents a group of formula: HO—(CH$_2$)$_n$—, q' and p' are integers of from 0 to 3 and n is an integer of from 0 to 6, which is reduced catalytically and halogenated to yield a compound (V):

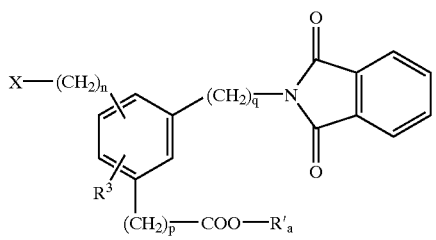

(V)

wherein R$^3$, n, p and q are as defined for formula (I), R'$_a$ represents a linear or branched (C$_1$–C$_6$)alkyl group and X represents a halogen atom, which compound of formula (V)

either, when m=1, is subjected to the nucleophilic attack of a compound of formula:

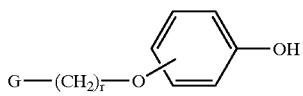

to yield a compound of formula (VI):

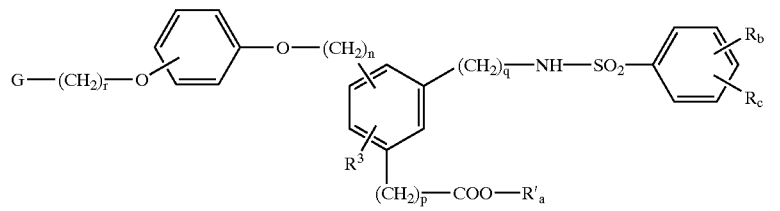

(VI)

in which formulae G, R$^3$, n, p, q and r are as defined for formula (I) and R'$_a$ represents a linear or branched (C$_1$–C$_6$)alkyl group, which is deprotected by cleavage of the phthalimido group in the presence of hydrazine to yield the corresponding amine which, in turn, is reacted with an optionally substituted benzenesulphonyl halide of formula:

$$X-SO_2-\underset{R_c}{\overset{R_b}{\text{Ar}}}$$

wherein X represents a halogen atom to yield a compound of formula (I/b), a particular case of the compounds of formula (I):

(I/b)

[structure of I/b]

wherein G, R$_b$, R$_c$, R$^3$, n, p, q and r are as defined for formula (I) and R'$_a$ represents a linear or branched (C$_1$–C$_6$)alkyl group, or, when m=0 and n=1, is subjected to the action of a compound of formula

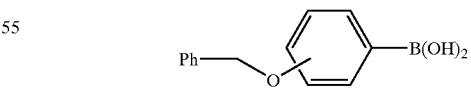

to yield, after debenzylation, a compound of formula (VII):

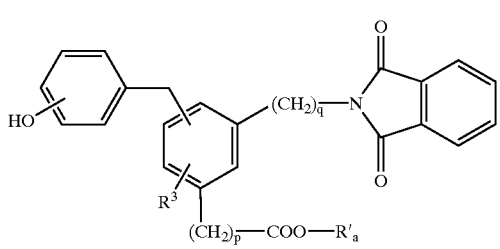

(VII)

wherein $R^3$, p and q are as defined for formula (I) and $R'_a$ represents a linear or branched $(C_1-C_6)$alkyl group,

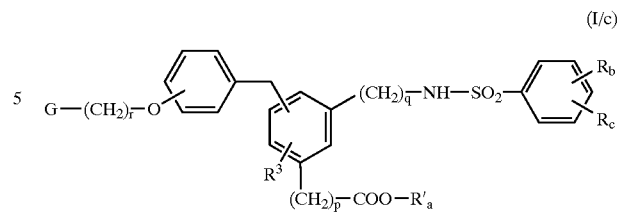

(I/c)

wherein G, $R_b$, $R_c$, $R^3$, p, q and r are as defined for formula (I) and $R'_a$ represents a linear or branched $(C_1-C_6)$alkyl group, which compounds of formula (I/a), (I/b) or (I/c) may be subjected to hydrolysis of the ester function, in acidic or basic medium according to the reactive groups present in the molecule, to yield a compound of formula (I/d):

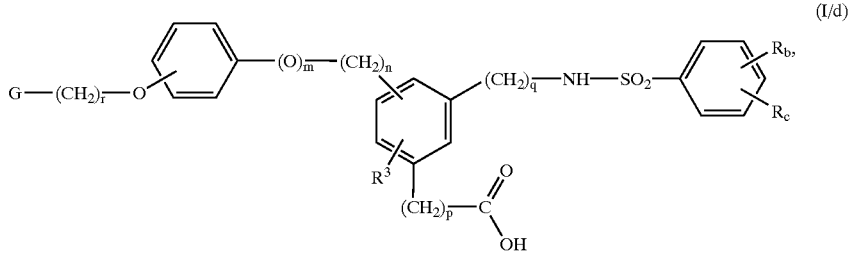

(I/d)

a particular case of the compounds of formula (I) wherein G, $R_b$, $R_c$, $R^3$, m, n, p, q and r are as defined for formula (I), which compounds (I/a), (I/b), (I/c) and (I/d) constitute the totality of the compounds of formula (I) and:
  may, if desired, be purified according to a conventional purification technique,
  are optionally separated into their stereoisomers according to a conventional separation technique,
  are, if desired, converted into their addition salts with a pharmaceutically acceptable acid or base, it being understood that, at any point considered appropriate during the course of the process described above, the carboxylic acid function may be esterified or the carboxylic ester function may be hydrolysed to the corresponding acid, which may be converted again to a different ester as required by the synthesis.

The present invention relates also to pharmaceutical compositions comprising as active ingredient at least one compound of formula (I), alone or in combination with one or more pharmaceutically acceptable, inert, non-toxic excipients or carriers.

Amongst the pharmaceutical compositions according to the invention there may be mentioned more especially those which are suitable for oral, parenteral or nasal administration, tablets or dragees, sublingual tablets, gelatin capsules, lozenges, suppositories, creams, ointments, dermal gels, etc.

The useful dosage varies in accordance with the age and weight of the patient, the nature and the severity of the disorder and also the administration route, which may be oral, nasal, rectal or parenteral. Generally, the unit dosage ranges from 0.1 mg to 500 mg for a treatment of from 1 to 3 administrations per 24 hours.

The following Examples illustrate the invention and do not limit it in any way. The structures of the described which is condensed in basic medium with a halide of formula G—(CH$_2$)$_r$—X wherein X represents a halogen atom to yield a compound of formula (VIII):

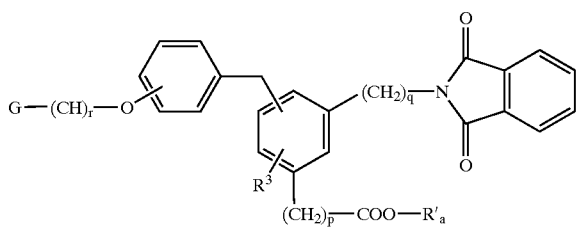

(VIII)

wherein G, $R^3$, p, q and r are as defined for formula (I) and $R'_a$ represents a linear or branched $(C_1-C_6)$alkyl group, which is deprotected by cleavage of the phthalimido group in the presence of hydrazine to yield the corresponding amine which, in turn, is reacted with an optionally substituted benzenesulphonyl halide of formula:

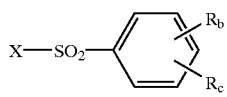

to yield a compound of formula (I/c), a particular case of the compounds (I):

compounds have been confirmed by customary spectroscopic and spectrometric techniques.

The starting materials employed are known products or products prepared according to known procedures.

Preparation A tert-Butyl (2E)-3-{3-[(E)-2-(1,3-dioxo-1,3-dihydro-2H-isoindol-2-yl)ethenyl]-5-[(E)-2-(2-hydroxyphenyl)ethenyl]phenyl}-2-propenoate Step a: 3,5-Dibromobenzaldehyde 0.222 mol of a solution of n-butyllithium in hexane is added dropwise at −80° C. to 0.222 mol of 1,3,5-tribromobenzene in 1.8 liters of ethyl ether. The reaction mixture is stirred at −80° C. for one hour. A solution of 0.222 mol of N,N-dimethylformamide in 50 ml of ethyl ether is slowly added. The temperature is maintained at −80° C. for one hour, before being brought to ambient temperature. Stirring is carried out for one night. 450 ml of 1N hydrochloric acid are added. The reaction mixture is extracted with ether. The organic phases are collected and dried over magnesium sulphate. After filtration and removal of the solvents by evaporation, the crude product is purified by chromatography on a silica column (eluant: cyclohexane/ethyl acetate: 95/5).

Step b: 2-[(E)-2-(3,5-Dibromophenyl)ethenyl]phenol 0.474 mol of a solution of n-butyllithium in hexane is added at +5° C. to 0.237 mol of (2-hydroxybenzyl)(triphenyl)phosphonium bromide in 1.2 liters of THF. The reaction mixture is maintained at +5° C. for one hour and then 0.21 mol of the compound obtained in the above Step dissolved in 360 ml of THF is added dropwise. The reaction mixture is slowly brought to ambient temperature and then hydrolysed and extracted with ethyl ether. The organic phases are collected and dried over magnesium sulphate. After filtration and removal of the solvents by evaporation, the crude product is purified by chromatography on a silica column (eluant: cyclohexane/ethyl acetate: 95/5).

Step c: 3-Bromo-5-[(E)-2-(2-hydroxyphenyl)ethenyl]benzaldehyde 0.378 mol of a solution of n-butyllithium in hexane is slowly added at −80° C. to 0.172 mol of the compound obtained in the above Step in 3 liters of ethyl ether. The reaction mixture is maintained at −80° C. for one hour and then 0.172 mol of N,N-dimethylformamide dissolved in 100 ml of ether is slowly added. The reaction mixture is maintained at that temperature for one hour and is then brought to +10° C. to be hydrolysed by a 1N hydrochloric acid solution. The mixture is extracted with ethyl ether, and the organic phases are collected and dried over magnesium sulphate. After filtration and removal of the solvents by evaporation, the crude product is purified by chromatography on silica (eluant: cyclohexane/ethyl acetate: 90/10).

Step d: tert-Butyl (2E)-3-{3-bromo-5-[(E)-2-(2-hydroxyphenyl)ethenyl]phenyl}-2-proenoate 0.3 mol of tert-butyl (triphenylphosphoranylidene)acetate is added to 0.15 mol of the compound obtained in the above Step in 2 liters of toluene. The reaction mixture is heated at reflux for 2 hours. The solvents are evaporated off and the crude product is purified by chromatography on a silica column (eluant: cyclohexane/ethyl acetate: 85/15).

Step e: tert-Butyl (2E)-3-{3-[(E)-2-(1,3-dioxo-1,3-dihydro-2H-isoindol-2-yl)ethenyl]-5-[(E)-2-(2-hydroxyphenyl)ethenyl]phenyl}-2-propenoate 0.1607 mol of the compound obtained in the above Step, 0.016 mol of palladium acetate, 0.032 mol of tris(2-methylphenyl)phosphine, 0.402 mol of diisopropylamine and 0.1607 mol of vinylphthalimide are added in succession to 2.5 liters of N,N-dimethylformamide and 10 ml of water.

The reaction mixture is heated at reflux for 3 hours and then brought to ambient temperature. After hydrolysis, the mixture is adjusted to pH 4 using a dilute hydrochloric acid solution and then extracted with dichloromethane. The organic phases are collected and dried over magnesium sulphate. After filtration and removal of the solvents by evaporation, the crude product is purified by chromatography on silica (eluant: cyclohexane/ethyl acetate: 70/30).

Preparation B tert-Butyl (2E)-3-[3-[(E)-2-(1,3-dioxo-1,3-dihydro-2H-isoindol-2-yl)ethenyl]-5-(hydroxymethyl)phenyl]-2-propenoate Step a: 3,5-Dibromobenzaldehyde The product is obtained in accordance with the same procedure as that described in Preparation A, Step a.

Step b: (3,5-Dibromophenyl)methanol 0.506 mol of sodium borohydride is added in portions to 0.3 mol of the compound obtained in the above Step in 650 ml of methanol and 200 ml of THF while maintaining the temperature at +30° C. After stirring for 4 hours, 300 ml of a saturated NaHCO₃ solution are added. The solvents are evaporated off. The solid obtained is filtered off, washed with water and dried.

Step c: 3-Bromo-5-(hydroxymethyl)benzaldehyde 0.628 mol of n-butyllithium is added at −80° C. to 0.285 mol of the compound obtained in the above Step in 2.3 liters of ether. The reaction mixture is maintained at that temperature for 4 hours 30 minutes. 22 ml of DMF dissolved in 100 ml of ether are added at −80° C. The mixture is maintained at −80° C. for 1 hour before being allowed to return to a temperature of +10° C. A 1N hydrochloric acid solution is added until an acid pH is obtained. The mixture is decanted, extracted with ethyl ether and dried over magnesium sulphate. The crude product is purified by chromatography (eluant: cyclohexane/ethyl acetate: 80/20).

Step d: tert-Butyl (2E)-3-[3-bromo-5-(hydroxymethyl)phenyl]-2-propenoate 0.35 mol of tert-butyl (triphenylphosphoranylidene) acetate is added to 0.175 mol of the compound obtained in the above Step in 1.65 liters of toluene. The reaction mixture is heated at reflux for 3 hours. The solvents are evaporated off. The crude product is taken up in isopropyl ether and heated at reflux for 1 hour. After cooling slowly, the precipitate is filtered off. The filtrate is evaporated and the crude product is purified by chromatography on a silica column (eluant: cyclohexane/ethyl acetate: 85/15).

Step e: tert-Butyl (2E)-3-[3-[(E)-2-(1,3-dioxo-1,3-dihydro-2H-isoindol-2-yl)ethenyl]-5-(hydroxymethyl)phenyl]-2-propenoate The procedure is identical to that used in Preparation A, Step e.

Preparation C tert-Butyl (2E)-3-{3-{(2E)-3-[2-(benzyloxy)phenyl]-2-propenyl}-5-[(E)-2-(1,3-dioxo-1,3-dihydro-2H-isoindol-2-yl)ethenyl]phenyl}-2-propenoate Step a: (3,5-Dibromobenzyl)(triphenyl)phosphonium bromide 0.20 mol of triphenylphosphine hydrobromide is added in portions to 0.20 mol of the compound obtained in Preparation A, Step a, in 800 ml of acetonitrile. The mixture is heated at reflux for 24 hours and then cooled. The solvent is subsequently evaporated off and the precipitate is filtered off and then dried.

Step b: [2-(Benzyloxy)phenyl]acetaldehyde 0.104 mol of hydroxy-1-oxo-benzo[d][1,2]iodoxol-3-one is added to 0.08 mol of [2-(2-benzyloxy)phenyl]ethanol in 500 ml of tetrahydrofuran. The reaction mixture is heated at reflux for 2 hours and then cooled. The precipitate is filtered off and the filtrate is evaporated.

Step c: 1-{(2E)-3-[2-(Benzyloxy)phenyl]-2-propenyl}-3,5-dibromobenzene 0.13 mol of potassium tert-butoxide is added in portions to 0.13 mol of the compound obtained in Step a in 800 ml of tetrahydrofuran. The reaction mixture is stirred for 30 minutes at ambient temperature and then 0.066 mol of the compound obtained in the above Step is added. After stirring for 12 hours, 150 ml of water are added and then extraction is carried out with dichloromethane. The organic phases are collected and dried over magnesium sulphate. The product is purified by chromatography on silica (eluant: cyclohexane/dichloromethane: 80/20).

Step d: tert-Butyl (2E)-3-(3-{(2E)-3-[2-(benzyloxy)phenyl]-2-propenyl}-5-bromophenyl)-2-propenoate The procedure is identical to that used in Preparation A, Steps c and d.

Step e: tert-Butyl (2E)-3-{3-{(2E)-3-[2-(benzyloxy)phenyl]-2-propenyl}-5-[(E)-2-(1,3-dioxo-1,3-dihydro-2H-isoindol-2yl)ethenyl]phenyl}-2-propenoate The procedure is identical to that used in Preparation A, Step e.

EXAMPLE 1

3-[3-(2-{[(4-Chlorophenyl)sulphonyl]amino}ethyl)-5-(2-{2-[2-(dimethylamino)ethoxy]phenyl}ethyl)phenyl]propanoic acid Step a: tert-Butyl 3-{3-[2-(1,3-dioxo-1,3-dihydro-2H-isoindol-2-yl)ethyl]-5-[2-(2-hydroxphenyl)ethyl]phenyl}propanoate 5 mmol de chlorotris(triphenylphosphine)rhodium are added to 0.048 mol of the compound obtained in Preparation A, Step e, dissolved in 720 ml of ethanol. The reaction mixture is heated at +50° C. for 3 days under a hydrogen pressure of 6 atm. After returning to ambient temperature, the solvents are evaporated off and the crude product is purified by chromatography on a silica column (eluant: cyclohexane/ethyl acetate: 80/20).

Step b: tert-Butyl 3-{3-(2-{2-[2-(dimethylamino)ethoxy]phenyl}ethyl)-5-[2-(1,3-dioxo-1,3-dihydro-2H-isoindol-2-yl)ethyl]phenyl}propanoate 0.01 mol of the compound obtained in the above Step dissolved in 100 ml of toluene is slowly added to 0.01 mol of sodium hydride, washed beforehand with pentane, suspended in 100 ml of toluene. The reaction mixture is heated at reflux for 30 minutes and then 0.013 mol of 2-chloro-N,N-dimethylethanamine dissolved in 40 ml of toluene is slowly added. Refluxing is maintained for 7 hours. After returning to ambient temperature, the reaction mixture is hydrolysed and then extraction is carried out with ethyl ether. The organic phases are collected, washed with a 1N sodium hydroxide solution and dried over magnesium sulphate.

Step c. tert-Butyl 3-[3-(2-aminoethyl)-5-(2-{2-[2-(dimethylamino)ethoxy]-phenyl}ethyl)phenyl]propanoate 0.0115 mol of hydrazine monohydrate is added to 0.01 mol of the compound obtained in the above Step in 27 ml of methanol and 4.5 ml of water. The mixture is heated at reflux for 2 hours 30 minutes and then cooled. After the addition of 91 ml of a 1N potassium carbonate solution and 75 ml of dichloromethane, decanting is carried out, extraction is carried out once with dichloromethane, and the solvents are evaporated off. The crude product is purified by chromatography on a silica column (eluant: dichloromethane/methanol/ammonium hydroxide: 95/5/0.5).

Step d: tert-Butyl 3-[3-(2-{[(4-chlorophenyl)sulphonyl]amino}ethyl)-5-(2-{2-[2-(dimethylamino)ethoxy]phenyl}ethyl)phenyl]propanoate 0.005 mol of triethylamine is added to 0.005 mol of the compound obtained in the above Step in 50 ml of dichloromethane. The reaction mixture is cooled to +5° C. 0.005 mol of 4-chlorobenzenesulphonyl chloride is added. The reaction mixture is brought to ambient temperature and then stirred for 45 minutes before being hydrolysed. After extraction with dichloromethane and drying over magnesium sulphate, the solvents are evaporated off. The crude product is used in the following Step without further purification.

Step e: 3-[3-(2-{[(4-Chlorophenyl)sulphonyl]amino}ethyl)-5-(2-{2-[2-(dimethylamino)ethoxy]phenyl}ethyl)phenyl]propanoic acid 0.004 mol of the compound obtained in the above Step is dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The product is extracted with ethyl acetate. The organic phases are collected and dried over magnesium sulphate. The solvent is evaporated off.

Elemental microanalysis:

|  | C | H | N | S |
| --- | --- | --- | --- | --- |
| % calculated | 62.30 | 6.31 | 5.01 | 5.73 |
| % found | 61.92 | 6.43 | 4.85 | 5.38 |

EXAMPLE 2

3-[3-(2-{[(4-Chlorophenyl)sulphonyl]amino}ethyl)-5-(2-{2-[3-(dimethylamino)propoxy]phenyl}ethyl)phenyl]propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-(2-{2-[3-(dimethylamino)propoxy]phenyl}ethyl)-5-[2-(1,3-dioxo-1,3-dihydro-2H-isoindol-2-yl)ethyl]phenyl}propanoate The expected product is obtained in accordance with the procedure described in Example 1, Step b, with the replacement of 2-chloro-N,N-dimethylethanamine with N-(3-chloropropyl)-N,N-dimethylamine.

Step c: tert-Butyl 3-[3-(2-aminoethyl)-5-(2-{2-[3-(dimethylamino)propoxy]-phenyl}ethyl)phenyl]propanoate The experimental conditions for obtaining the product are identical to those used in Example 1, Step c.

Step d: tert-Butyl 3-(3-(2-{2-[3-(dimethylamino)propoxy]phenyl}ethyl)-5-{2-[(phenylsulphonyl)amino]ethyl}phenyl)propanoate The experimental conditions for obtaining the product are identical to those used in Example 1, Step d.

Step e: 3-[3-(2-{[(4-Chlorophenyl)sulphonyl]amino}ethyl)-5-(2-{2-[3-(dimethylamino)propoxy]phenyl}ethyl)phenyl]propanoic acid 0.004 mol of the compound obtained in the above Step are dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The product is purified by precipitation procedures, filtration and washing with water and is finally dried.

Elemental microanalysis:

|  | C | H | Cl | N | S |
|---|---|---|---|---|---|
| % calculated | 62.87 | 6.51 | 6.19 | 4.89 | 5.59 |
| % found | 62.76 | 6.58 | 6.30 | 4.81 | 5.51 |

EXAMPLE 3

3-[3-(2-{[(4-Chlorophenyl)sulphonyl]amino}ethyl)-5-(2-{2-[2-(1-pyrrolidinyl)ethoxy]phenyl}ethyl)phenyl]propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-[3-[2-(1,3-dioxo-1,3-dihydro-2H-isoindol-2-yl)ethyl]-5-(2-{2-[2-(1-pyrrolidinyl)ethoxy]phenyl}ethyl)phenyl]propanoate The expected product is obtained in accordance with the procedure described in Example 1, Step b, with the replacement of 2-chloro-N,N-dimethylethanamine with 1-(2-chloroethyl)pyrrolidine.

Step c: tert-Butyl 3-[3-(2-aminoethyl)-5-(2-{2-[2-(1-pyrrolidinyl)ethoxy]-phenyl}ethyl)phenyl]propanoate The experimental conditions for obtaining the product are identical to those used in Example 1, Step c.

Step d: tert-Butyl 3-[3-(2-{[(4-chlorophenyl)sulphonyl]amino}ethyl)-5-(2-{2-[2-(1-pyrrolidinyl)ethoxy]phenyl}ethyl)phenyl]propanoate The experimental conditions for obtaining the product are identical to those used in Example 1, Step d.

Step e: 3-[3- (2-{[(4-Chlorophenyl)sulphonyl]amino}ethyl)-5-(2-{2-[2-(1-pyrrolidinyl)ethoxy]phenyl}ethyl)phenyl] propanoic acid 0.004 mol of the compound obtained in the above Step is dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The product is extracted with ethyl acetate. The organic phases are collected and dried over magnesium sulphate. The solvent is evaporated off. The product is purified by chromatography on a silica column (eluant: dichloromethane/methanol/ammonium hydroxide: 90/10/1).

Elemental microanalysis:

|  | C | H | Cl | N | S |
|---|---|---|---|---|---|
| % calculated | 63.63 | 6.37 | 6.06 | 4.79 | 5.48 |
| % found | 63.30 | 6.47 | 6.30 | 4.83 | 5.23 |

EXAMPLE 4

3-[3-(2-{[(4-Chlorophenyl)sulphonyl]amino}ethyl)-5-(2-{2-[2-(4-morpholinyl)ethoxy]phenyl}ethyl)phenyl]propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-[3-[2-(1,3-dioxo-1,3-dihydro-2H-isoindol-2-yl)ethyl]-5-(2-{2-[2-(4-morpholinyl)ethoxy]phenyl}ethyl)phenyl]propanoate The expected product is obtained in accordance with the procedure described in Example 1, Step b, with the replacement of 2-chloro-N,N-dimethylethanamine with 4-(2-chloroethyl)morpholine.

Step c: tert-Butyl 3-[3-(2-aminoethyl)-5-(2-{2-[2-(4-morpholinyl)ethoxy]-phenyl}ethyl)phenyl]propanoate The experimental conditions for obtaining the product are identical to those used in Example 1, Step c.

Step d: tert-Butyl 3-[3-(2-{[(4-chlorophenyl)sulphonyl]amino}ethyl)-5-(2-{2-[2-(4-morpholinyl)ethoxy]phenyl}ethyl)phenyl]propanoate The experimental conditions for obtaining the product are identical to those used in Example 1, Step d.

Step e: 3-[3-(2-{[(4-Chlorophenyl)sulphonyl]amino}ethyl)-5-(2-{2-[2-(4-morpholinyl)ethoxy]phenyl}ethyl)phenyl] propanoic acid The expected product is obtained in accordance with the same procedure as that described in Example 1, Step e.

Elemental microanalysis:

|  | C | H | Cl | N | S |
|---|---|---|---|---|---|
| % calculated | 61.94 | 6.20 | 5.90 | 4.66 | 5.33 |
| % found | 61.82 | 6.26 | 6.21 | 4.70 | 5.10 |

EXAMPLE 5

3-[3-(2-{[(4-Chlorophenyl)sulphonyl]amino}ethyl)-5-(2-{4-[2-(dimethylamino)ethoxy]phenyl}ethyl)phenyl]propanoic acid Step a: tert-Butyl 3-{3-[2-(1,3-dioxo-1,3-dihydro-2H-isoindol-2-yl)ethyl]-5-[2-(4-hydroxyphenyl)ethyl]phenyl}propanoate The experimental procedure is identical to that of Example 1, Step a, using (4-hydroxybenzyl)(triphenyl)phosphonium bromide instead of (2-hydroxybenzyl)(triphenyl)phosphonium bromide as Wittig reagent in Preparation A, Step b.

Step b: tert-Butyl 3-{3-(2-{4-[2-(dimethylamino)ethoxy]phenyl}ethyl)-5-[2-(1,3-dioxo-1,3-dihydro-2H-isoindol-2-yl)ethyl]phenyl}propanoate The expected product is obtained in accordance with the procedure described in Example 1, Step b.

Step c: tert-Butyl 3-[3-(2-aminoethyl)-5-(2-{4-[2-(dimethylamino)ethoxy]-phenyl}ethyl)phenyl]propanoate The experimental conditions for obtaining the product are identical to those used in Example 1, Step c.

Step d: tert-Butyl 3-[3-(2-{[(4-chlorophenyl)sulphonyl]amino}ethyl)-5-(2-{4-[2-(dimethylamino)ethoxy]phenyl}ethyl)phenyl]propanoate The experimental conditions for obtaining the product are identical to those used in Example 1, Step d.

Step e: 3-[3-(2-{[(4-Chlorophenyl)sulphonyl]amino}ethyl)-5-(2-{4-[2-(dimethylamino)ethoxy]phenyl}ethyl)phenyl]propanoic acid The expected product is obtained in accordance with the same method as that described in Example 1, Step e, and purified with the aid of chromatography on a silica column (dichloromethane/methanol/ammonium hydroxide: 90/10/1).

Elemental microanalysis:

|  | C | H | Cl | N | S |
|---|---|---|---|---|---|
| % calculated | 62.30 | 6.31 | 6.34 | 5.01 | 5.73 |
| % found | 62.02 | 6.14 | 6.08 | 5.03 | 5.36 |

EXAMPLE 6

3-{3-(2-{[(4-Chlorophenyl)sulphonyl]amino}ethyl)-5-[2-(2-{2-[4-(4-fluorophenyl)-1-piperazinyl]ethoxy}phenyl)ethyl]phenyl}propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-[2-(1,3-dioxo-1,3-dihydro-2H-isoindol-2-yl)ethyl]-5-[2-(2-{2-[4-(4-fluorophenyl)-1-piperazinyl]ethoxy}phenyl)ethyl]phenyl}-propanoate The expected product is obtained in accordance with the procedure described in Example 1, Step b, with the replacement of 2-chloro-N,N-dimethylethanamine with 1-(2-chloroethyl)-4-(4-fluorophenyl)piperazine.

Step c: tert-Butyl 3-{3-(2-aminoethyl)-5-[2-(2-{2-[4-(4-fluorophenyl)-1-piperazinyl]ethoxy}phenyl)ethyl]phenyl}propanoate The experimental conditions for obtaining the product are identical to those used in Example 1, Step c.

Step d: tert-Butyl 3-{3-(2-{[(4-chlorophenyl)sulphonyl]amino}ethyl)-5-[2-(2-{2-[4-(4-fluorophenyl)-1-piperazinyl]ethoxy}phenyl)ethyl]phenyl}-propanoate The experimental conditions for obtaining the product are identical to those used in Example 1, Step d.

Step e: 3-{3-(2-{[(4-Chlorophenyl)sulphonyl]amino}ethyl)-5-[2-(2-{2-[4-(4-fluorophenyl)-1-piperazinyl]ethoxy}phenyl)ethyl]phenyl}propanoic acid The expected product is obtained in accordance with the same method as that described in Example 3, Step e, and purified with the aid of chromatography on a silica column (dichloromethane/methanol/ammonium hydroxide: 97/3/0.3).

Elemental microanalysis:

|  | C | H | Cl | N | S |
|---|---|---|---|---|---|
| % calculated | 64.01 | 5.95 | 5.11 | 6.05 | 4.62 |
| % found | 63.58 | 6.17 | 5.42 | 5.95 | 4.31 |

EXAMPLE 7

3-{3-(2-{[(4-Chlorophenyl)sulphonyl]amino}ethyl)-5-[2-(2-{3-[4-(4-fluorophenyl)-1-piperazinyl]propoxy}phenyl)ethyl]phenyl}-propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-[2-(1,3-dioxo-1,3-dihydro-2H-isoindol-2-yl)ethyl]-5-[2-(2-{3-[4-(4-fluorophenyl)-1-piperazinyl]propoxy}phenyl)ethyl]phenyl}-propanoate The expected product is obtained in accordance with the procedure described in Example 1, Step b, with the replacement of 2-chloro-N,N-dimethylethanamine with 1-(3-chloropropyl)-4-(4-fluorophenyl)piperazine.

Step c: tert-Butyl 3-{3-(2-aminoethyl)-5-[2-(2-{3-[4-(4-fluorophenyl)-1-piperazinyl]propoxy}phenyl)ethyl]phenyl}propanoate The experimental conditions for obtaining the product are identical to those used in Example 1, Step c.

Step d: tert-Butyl 3-{3-(2-{[(4-chlorophenyl)sulphonyl]amino}ethyl)-5-[2-(2-{3-[4-(4-fluorophenyl)-1-piperazinyl]propoxy}phenyl)ethyl]phenyl}-propanoate The experimental conditions for obtaining the product are identical to those used in Example 1, Step d.

Step e: 3-{3-(2-{[(4-Chlorophenyl)sulphonyl]amino}ethyl)-5-[2-(2-{3-[4-(4-fluorophenyl)-1-piperazinyl]propoxy}phenyl)ethyl]phenyl}propanoic acid The expected product is obtained in accordance with the same procedure as that described in Example 1, Step e.

Elemental microanalysis:

|  | C | H | Cl | N | S |
|---|---|---|---|---|---|
| % calculated | 64.44 | 6.12 | 5.01 | 5.93 | 4.53 |
| % found | 63.49 | 6.00 | 5.09 | 5.84 | 4.13 |

EXAMPLE 8

3-[3-(2-{[(4-Chlorophenyl)sulphonyl]amino}ethyl)-5-(2-{2-[4-(dimethylamino)butoxy]phenyl}ethyl)phenyl]propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-(2-{2-[4-(dimethylamino)butoxy]phenyl}ethyl)-5-[2-(1,3-dioxo-1,3-dihydro-2H-isoindol-2-yl)ethyl]phenyl}propanoate The expected product is obtained in accordance with the procedure described in Example 1, Step b, with the replacement of 2-chloro-N,N-dimethylethanamine with N-(4-chlorobutyl)-N,N-dimethylamine.

Step c: tert-Butyl 3-[3-(2-aminoethyl)-5-(2-{2-[4-(dimethylamino)butoxy]-phenyl}ethyl)phenyl]propanoate The experimental conditions for obtaining the product are identical to those used in Example 1, Step c.

Step d: tert-Butyl 3-[3-(2-{[(4-chlorophenyl)sulphonyl]amino}ethyl)-5-(2-{2-[4-(dimethylamino)butoxy]phenyl}ethyl)phenyl]propanoate The experimental conditions for obtaining the product are identical to those used in Example 1, Step d.

Step e: 3-[3-(2-{[(4-Chlorophenyl)sulphonyl]amino}ethyl)-5-(2-{2-[4-(dimethylamino)butoxy]phenyl}ethyl)phenyl]propanoic acid The expected product is obtained in accordance with the same method as that described in Example 3, Step e, with the exception of the eluant in the purification by chromatography on a silica column (dichloromethane/methanol/ammonium hydroxide: 97/3/0.3).
Elemental microanalysis:

|  | C | H | Cl | N | S |
|---|---|---|---|---|---|
| % calculated | 63.41 | 6.69 | 6.04 | 4.77 | 5.46 |
| % found | 63.38 | 6.96 | 6.12 | 4.74 | 5.21 |

EXAMPLE 9

3-{3-(2-{[(4-Chlorophenyl)sulphonyl]amino}ethyl)-5-[2-(2-{2-[4-(6-fluoro-1,2-benzisoxazol-3-yl)-1-piperidyl]ethoxy}phenyl)ethyl]-phenyl}propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate
The experimental procedure is identical to that of Example 1, Step a.
Step b: tert-Butyl 3-{3-[2-(1,3-dioxo-1,3-dihydro-2H-isoindol-2-yl)ethyl]-5-[2-(2-{2-[4-(6-fluoro-1,2-benzisoxazol-3-yl)-1-piperidyl]ethoxy}phenyl)-ethyl]phenyl}propanoate
The expected product is obtained in accordance with the procedure described in Example 1, Step b, with the replacement of 2-chloro-N,N-dimethylethanamine with 3-[1-(2-chloroethyl)-4-piperidyl]-6-fluoro-1,2-benzisoxazole.
Step c: tert-Butyl 3-{3-(2-aminoethyl)-5-[2-(2-{2-[4-(6-fluoro-1,2-benzisoxazol-3-yl)-1-piperidyl]ethoxy}phenyl)ethyl]phenyl}propanoate
The experimental conditions for obtaining the product are identical to those used in Example 1, Step c.
Step d: tert-Butyl 3-{3-(2-{[(4-chlorophenyl)sulphonyl]amino}ethyl)-5-[2-(2-{2-[4-(6-fluoro-1,2-benzisoxazol-3-yl)-1-piperidyl]ethoxy}phenyl)ethyl]phenyl}propanoate
The experimental conditions for obtaining the product are identical to those used in Example 1. Step d.
Step e: 3-{3-(2-{[(4-Chlorophenyl)sulphonyl]amino}ethyl)-5-[2-(2-{2-[4-(6-fluoro-1,2-benzisoxazol-3-yl)-1-piperidyl]ethoxy}phenyl)ethyl]phenyl}-propanoic acid
0.004 mol of the compound obtained in the above Step is dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The crude product is extracted with ethyl acetate. The organic phases are collected and dried over magnesium sulphate. The crude product is purified by chromatography on a silica column (eluant: dichloromethane/methanol: 95/5).
Elemental microanalysis:

|  | C | H | Cl | N | S |
|---|---|---|---|---|---|
| % calculated | 63.79 | 5.63 | 4.83 | 5.72 | 4.37 |
| % found | 63.74 | 5.82 | 5.04 | 5.66 | 4.01 |

EXAMPLE 10

3-[3-[2-(2-{2-[4-(1,2-Benzisothiazol-3-yl)-1-piperazinyl]ethoxy}-phenyl)ethyl]-5-(2-{[(4-chlorophenyl)sulphonyl]amino}ethyl)-phenyl] propanoic acid hydrochloride Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate
The experimental procedure is identical to that of Example 1, Step a.
Step b: tert-Butyl 3-{3-[2-(2-{2-[4-(1,2-benzisothiazol-3-yl)-1-piperazinyl]ethoxy}phenyl)ethyl]-5-[2-(1,3-dioxo-1,3-dihydro-2H-isoindol-2-yl)ethyl]phenyl}propanoate
The expected product is obtained in accordance with the procedure described in Example 1, Step b, with the replacement of 2-chloro-N,N-dimethylethanamine with 3-[4-(2-chloroethyl)-4-piperazinyl]-1,2-benzisothiazole.
Step c: tert-Butyl 3-{3-(2-aminoethyl)-5-[2-(2-{2-[4-(1,2-benzisothiazol-3-yl)-1-piperazinyl]ethoxy}phenyl)ethyl]phenyl}propanoate
The experimental conditions for obtaining the product are identical to those used in Example 1, Step c.
Step d: tert-Butyl 3-[3-[2-(2-{2-[4-(1,2-benzisothiazol-3-yl)-1-piperzinyl]-ethoxy}phenyl)ethyl]-5-(2-{[(4-chlorophenyl)sulphonyl]amino}ethyl)-phenyl]propanoate
The experimental conditions for obtaining the product are identical to those used in Example 1, Step d.
Step e: 3-[3-[2-(2-{2-[4-(1,2-Benzisothiazol-3-yl)-1-piperazinyl]ethoxy}phenyl)-ethyl]-5-(2-{[(4-chlorophenyl)sulphonyl]amino}ethyl)phenyl]propanoic acid hydrochloride
0.004 mol of the compound obtained in the above Step is dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The expected product is filtered off, washed with water and then taken up in dichloromethane. After the addition of one equivalent of a 1N hydrochloric acid solution in ethyl ether, the precipitated product is filtered off.
Elemental microanalysis:

|  | C | H | Cl | N | S |
|---|---|---|---|---|---|
| % calculated | 59.29 | 5.50 | 4.61 | 7.28 | 8.33 |
| % found | 59.06 | 5.57 | 4.70 | 7.13 | 7.97 |

EXAMPLE 11

3-{3-(2-{[(4-Chlorophenyl)sulphonyl]amino}ethyl)-5-[2-(2-{2-[4-(6-fluoro-1,2-benzisothiazol-3-yl)-1-piperidyl]ethoxy}phenyl)ethyl]-phenyl}propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate
The experimental procedure is identical to that of Example 1, Step a.
Step b: tert-Butyl 3-{3-[2-(1,3-dioxo-1,3-dihydro-2H-isoindol-2-yl)ethyl]-5-[2-(2-{2-[4-(6-fluoro-1,2-benzisothiazol-3-yl)-1-piperidyl]ethoxy}phenyl)-ethyl]phenyl}propanoate The expected product is obtained in accordance with the procedure described in Example 1, Step b, with the replacement of 2-chloro-N,N-dimethylethanamine with 3-[1-(2-chloroethyl)-4-piperidyl]-6-fluoro-1,2-benzisothiazole.

Step c: tert-Butyl 3-{3-(2-aminoethyl)-5-[2-(2-{2-[4-(6-fluoro-1,2-benzisothiazol-3-yl)-1-piperidyl]ethoxy}phenyl)ethy]phenyl}propanoate The experimental conditions for obtaining the product are identical to those used in Example 1, Step c.

Step d: tert-Butyl 3-{3-(2-{[(4-chlorophenyl)sulphonyl]amino}ethyl)-5-[2-(2-{2-[4-(6-fluoro-1,2-benzisothiazol-3-yl)-1-piperidyl]ethoxy}phenyl)ethyl]phenyl}propanoate The experimental conditions for obtaining the product are identical to those used in Example 1, Step d.

Step e: 3-{3-(2-{[(4-Chlorophenyl)sulphonyl]amino}ethyl)-5-[2-(2-{2-[4-(6-fluoro-1,2-benzisothiazol-3-yl)-1-piperidyl]ethoxy}phenyl)ethyl]phenyl}propanoic acid 0.004 mol of the compound obtained in the above Step is dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The crude product is purified by precipitation, and then after filtration is washed with ether. The expected product is purified by chromatography on a silica column (eluant: dichloromethane/methanol: 97/3).

Elemental microanalysis:

|  | C | H | Cl | N | S |
| --- | --- | --- | --- | --- | --- |
| % calculated | 62.43 | 5.51 | 4.72 | 5.60 | 8.55 |
| % found | 62.19 | 5.60 | 4.86 | 5.58 | 8.08 |

EXAMPLE 12

3-[3-[2-(2-{3-[4-(1,2-Benzisothiazol-3-yl)-1-piperazinyl]propoxy}-phenyl)ethyl]-5-(2-{[(4-chlorophenyl)sulphonyl]amino}ethyl)phenyl] propanoic acid hydrochloride Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-[2-(2-{3-[4-(1,2-benzisothiazol-3-yl)-1-piperazinyl]propoxy}phenyl)ethyl]-5-[2-(1,3-dioxo-1,3-dihydro-2H-isoindol-2-yl)ethyl]phenyl}propanoate The expected product is obtained in accordance with the procedure described in Example 1, Step b, with the replacement of 2-chloro-N,N-dimethylethanamine with 3-[4-(3-chloropropyl)-1-piperazinyl]-1,2-benzisothiazole.

Step c: tert-Butyl 3-{3-(2-aminoethyl)-5-[2-(2-{3-[4-(1,2-benzisothiazol-3-yl)-1-piperazinyl]propoxy}phenyl)ethyl]phenyl}propanoate The experimental conditions for obtaining the product are identical to those used in Example 1, Step c.

Step d: tert-Butyl 3-[3-[2-(2-{3-[4-(1,2-benzisothiazol-3-yl)-1-piperazinyl]propoxy}phenyl)ethyl]-5-(2-{[(4-chlorophenyl)sulphonyl]amino}ethyl)phenyl]propanoate The experimental conditions for obtaining the product are identical to those used in Example 1, Step d.

Step e: 3-[3-[2-(2-{3-[4-(1,2-Benzisothiazol-3-yl)-1-piperazinyl]propoxy}phenyl)ethyl]-5-(2-{[(4-chlorophenyl)sulphonyl]amino}ethyl)phenyl]propanoic acid hydrochloride 0.004 mol of the compound obtained in the above Step are dissolved in 25 ml of trifluoroacetic acid. The reaction mixture is stirred for 30 minutes and then the trifluoroacetic acid is evaporated off. The crude product is taken up in a 2N sodium hydroxide solution. After extraction with ethyl ether, the aqueous phase is acidified with acetic acid until a pH of 4–5 is obtained. The crude product is purified by precipitation and then after filtration is washed with ether. The expected product is purified by chromatography on a silica column (eluant: dichloromethane/methanol/ammonium hydroxide: 95/5/0.5). The expected product is taken up in dichloromethane. After the addition of one equivalent of a 1N hydrochloric acid solution in ether, the precipitated product is filtered off.

Elemental microanalysis:

|  | C | H | Cl | N | S |
| --- | --- | --- | --- | --- | --- |
| % calculated | 59.76 | 5.66 | 9.05 | 7.15 | 8.18 |
| % found | 59.76 | 5.67 | 9.05 | 6.97 | 7.54 |

EXAMPLE 13

3-{3-(2-{[(4-Chlorophenyl)sulphonyl]amino}ethyl)-5-[2-(2-{3-[4-(6-fluoro-1,2-benzisoxazol-3-yl)-1-piperidyl]propoxy}phenyl)ethyl]phenyl}propanoic acid Step a: tert-Butyl 3-{3-[2-(1,3-dioxo-1,3-dihydro-2H-isoindol-2-yl)ethyl]-5-[2-(2-hydroxyphenyl)ethyl]phenyl}propanoate The experimental procedure is identical to that of Example 1, Step a.

Step b: tert-Butyl 3-{3-[2-(1,3-dioxo-1,3-dihydro-2H-isoindol-2-yl)ethyl]-5-[2-(2-{3-[4-(6-fluoro-1,2-benzisoxazol-3-yl)-1-piperidyl]propoxy}phenyl)ethyl]phenyl}propanoate The expected product is obtained in accordance with the procedure described in Example 1, Step b, with the replacement of 2-chloro-N,N-dimethylethanamine with 3-[1-(3-chloropropyl)-4-piperidyl]-6-fluoro-1,2-benzisoxazole.

Step c: tert-Butyl 3-{3-(2-aminoethyl)-5-[2-(2-{3-[4-(6-fluoro-1,2-benzisoxazol-3-yl)-1-piperidyl]propoxy}phenyl)ethyl]phenyl}propanoate The experimental conditions for obtaining the product are identical to those used in Example 1, Step c.

Step d: tert-Butyl 3-{3-(2-{[(4-chlorophenyl)sulphonyl]amino}ethyl)-5-[2-(2-{3-[4-(6-fluoro-1,2-benzisoxazol-3-yl)-1-piperidyl]propoxy}phenyl)ethyl]phenyl}propanoate The experimental conditions for obtaining the product are identical to those used in Example 1, Step d.

Step e: 3-{3-(2-{[4-Chlorophenyl)sulphonyl]amino}ethyl)-5-[2-(2-{3-[4-(6-fluoro-1,2-benzisoxazol-3-yl)-1-piperidyl]propoxy}phenyl)ethyl]phenyl}propanoic acid The expected product is obtained in accordance with the same method as that described in Example 8, Step e, with the exception of the eluant in the purification by chromatography on a silica column (dichloromethane/methanol/ammonium hydroxide: 95/5/0.5).

Elemental microanalysis:

|  | C | H | Cl | N | S |
|---|---|---|---|---|---|
| % calculated | 64.20 | 5.79 | 4.74 | 5.62 | 4.28 |
| % found | 63.89 | 5.95 | 4.41 | 5.46 | 4.12 |

EXAMPLE 14

3-[3-(2-{[(4-Chlorophenyl)sulphonyl]amino}ethyl)-5-({4-[2-(dimethylamino)ethoxy]phenoxy}methyl)phenyl]propanoic acid Step a: tert-Butyl 3-[3-[2-(1,3-dioxo-1,3-dihydro-2H-isoindol-2-yl)ethyl]-5-(hydroxymethyl)phenyl]propanoate Catalytic hydrogenation of the product of Preparation B, Step e, is carried out under the same experimental conditions as in Example 1, Step a.

Step b: tert-Butyl 3-{3-(bromomethyl)-5-[2-(1,3-dioxo-1,3-dihydro-2H-isoindol-2-yl)ethyl]phenyl}propanoate To 0.052 mol of the compound obtained in the above Step, dissolved in 320 ml of dichloromethane, there are added 0.063 mol of triphenylphosphine and then, slowly, a solution of 0.063 mol of carbon tetrabromide in 85 ml of dichloromethane, while maintaining the temperature below 30° C. The mixture is stirred for 15 hours and then concentrated to dryness. The crude product is purified by chromatography (eluant: cyclohexane/ethyl acetate: 80/20).

Step c: tert-Butyl 3-{3-({4-[2-(dimethylamino)ethoxy]phenoxy}methyl)-5-[2-(1,3-dioxo-1,3-dihydro-2H-isoindol-2-yl)ethyl]phenyl}propanoate 0.0083 mol of 4-[2-(dimethylamino)ethoxy]phenol suspended in 15 ml of toluene is added to 0.0196 mol of sodium hydride, washed beforehand with pentane, in 90 ml of toluene. The mixture is heated at reflux for 1 hour, and then 0.0064 mol of the compound obtained in the above Step dissolved in 90 ml of toluene is introduced. Refluxing is maintained for 4 hours. After the addition of water and extraction with ethyl ether, the organic phases are washed with a 1N sodium hydroxide solution and dried over magnesium sulphate. After filtration, the crude product is used without further purification.

Step d: 3-[3-(2-{[(4-Chlorophenyl)sulphonyl]amino}ethyl)-5-({4-[2-(dimethylamino)ethoxy]phenoxy}methyl)phenyl]propanoic acid Using as starting material the product synthesised above, the experimental conditions for deprotection of the amine, addition of benzenesulphonyl chloride and finally hydrolysis of the ester are identical to those used in Example 1, Step c, Step d and finally Step e, respectively.

Elemental microanalysis:

|  | C | H | Cl | N | S |
|---|---|---|---|---|---|
| % calculated | 59.94 | 5.93 | 6.32 | 4.99 | 5.71 |
| % found | 59.95 | 6.04 | 6.94 | 4.97 | 5.43 |

EXAMPLE 15

3-[3-(2-{[(4-Chlorophenyl)sulphonyl]amino}ethyl)-5-({2-[2-(dimethylamino)ethoxy]phenoxy}methyl)phenyl]propanoic acid Step a: tert-Butyl 3-[3-[2-(1,3-dioxo-1,3-dihydro-2H-isoindol-2-yl)ethyl]-5-(hydroxymethyl)phenyl]propanoate The experimental procedure is identical to that of Example 14, Step a.

Step b: tert-Butyl 3-{3-(bromomethyl)-5-[2-(1,3-dioxo-1,3-dihydro-2H-isoindol-2-yl)ethyl]phenyl}propanoate The experimental procedure is identical to that of Example 14, Step b.

Step c: tert-Butyl 3-{3-({2-[2-(dimethylamino)ethoxy]phenoxy}methyl)-5-[2-(1,3-dioxo-1,3-dihydro-2H-isoindol-2-yl)ethyl]phenyl}propanoate The expected product is obtained in accordance with the procedure described in Example 14, Step c, with the replacement of 4-[2-(dimethylamino)ethoxy]phenol with 2-[2-(dimethylamino)ethoxy]phenol.

Step d: 3-[3-(2-{[(4-Chlorophenyl)sulphonyl]aminoy}ethyl)-5-({2-[2-(dimethylamino)ethoxy]phenoxy}methyl)phenyl]propanoic acid The experimental procedure is identical to that of Example 14, Step d.

Elemental microanalysis:

|  | C | H | Cl | N | S |
|---|---|---|---|---|---|
| % calculated | 59.94 | 5.93 | 6.32 | 4.99 | 5.71 |
| % found | 60.34 | 6.16 | 6.77 | 4.91 | 5.31 |

EXAMPLE 16

3-[3-(2-{[(4-Chlorophenyl)sulphonyl]amino}ethyl)-5-({2-[3-(dimethylamino)propoxy]phenoxy}methyl)phenyl]propanoic acid Step a: tert-Butyl 3-[3-[2-(1,3-dioxo-1,3-dihydro-2H-isoindol-2-yl)ethyl]-5-(hydroxymethyl)phenyl]propanoate The experimental procedure is identical to that of Example 14, Step a.

Step b: tert-Butyl 3-{3-(bromomethyl)-5-[2-(1,3-dioxo-1,3-dihydro-2H-isoindol-2-yl)ethyl]phenyl}propanoate The experimental procedure is identical to that of Example 14, Step b.

Step c: tert-Butyl 3-{3-({2-[3-(dimethylamino)propoxy]phenoxy}methyl)-5-[2-(1,3-dioxo-1,3-dihydro-2H-isoindol-2-yl)ethyl]phenyl}propanoate The expected product is obtained in accordance with the procedure described in Example 14, Step c, with the replacement of 4-[2-(dimethylamino)ethoxy]phenol with 2-[3-(dimethylamino)propoxy]phenol.

Step d: 3-[3-(2-{[(4-Chlorophenyl)sulphonyl]amino}ethyl)-5-({2-[3-(dimethylamino)propoxy]phenoxy}methyl)phenyl]propanoic acid The experimental procedure is identical to that of Example 14, Step d.

Elemental microanalysis:

|  | C | H | Cl | N | S |
|---|---|---|---|---|---|
| % calculated | 60.56 | 6.13 | 6.16 | 4.87 | 5.58 |
| % found | 61.57 | 6.59 | 6.09 | 4.62 | 5.52 |

EXAMPLE 17

3-(3-(2-{[(4-Chlorophenyl)sulphonyl]amino}ethyl)-5-{2-[3-(dimethylamino)propoxy]benzyl}phenyl)propanoic acid hydrochloride Step a: tert-Butyl 3-{3-(bromomethyl)-5-[2-(1,3-dioxo-1,3-dihydro-2H-isoindol-2-yl)ethyl]phenyl}propanoate The experimental procedure is identical to that of Example 14, Step b.

Step b: tert-Butyl 3-{3-[2-(benzyloxy)benzyl]-5-[2-(1,3-dioxo-1,3-dihydro-2H-isoindol-2-yl)ethyl]phenyl}propanoate 0.017 mol of 2-benzyloxyphenylboronic acid, 34 ml of a 2M $Na_2CO_3$ solution and 0.85 mol of tetrakis (triphenylphosphine)palladium are added in succession to 0.017 mol of the compound obtained in the above Step dissolved in 130 ml of an 80/50 toluene/ethanol mixture. The reaction mixture is heated at reflux for 3 hours 30 minutes and then cooled. After the addition of water and toluene, the mixture is decanted and extracted 3 times with toluene. The organic phases are washed twice with a saturated NaCl solution and then dried over magnesium sulphate. After removal of the solvents by evaporation, the crude product is used without further purification.

Step c: tert-Butyl 3-[3-[2-(1,3-dioxo-1,3-dihydro-2H-isoindol-2-yl)ethyl]-5-(2-hydroxybenzyl)phenyl]propanoate 1.4 g of palladium dihydroxide are added to 0.0125 mol of the compound obtained in the above Step in 90 ml of a 50/40 ethanol/THF mixture. The mixture is placed in the presence of hydrogen at ambient temperature for 2 hours. The mixture is filtered and the solvent is evaporated off. The product is used without further purification.

Step d: tert-Butyl 3-{3-{2-[3-(dimethylamino)propoxy]benzyl}-5-[2-(1,3-dioxo-1,3-dihydro-2H-isoindol-2-yl)ethyl]phenyl}propanoate The experimental procedure is identical to that of Example 2, Step b.

Step e: 3-(3-(2-{[(4-Chlorophenyl)sulphonyl]amino}ethyl)-5-{2-[3-(dimethylamino)propoxy]benzyl}phenyl) propanoic acid hydrochloride Deprotection of the amine, addition of benzenesulphonyl chloride and finally hydrolysis of the ester are identical to the experimental methods used in Example 1, Step c, Step d and finally Step e, respectively.

Elemental microanalysis:

|  | C | H | Cl | N | S |
|---|---|---|---|---|---|
| % calculated | 60.32 | 6.21 | 9.21 | 4.85 | 5.55 |
| % found | 59.31 | 6.34 | 8.88 | 4.57 | 5.61 |

EXAMPLE 18

3-[3-(2-{[(4-Chlorophenyl)sulphonyl]amino}ethyl)-5-(3-{2-[3-(dimethylamino)propoxy]phenyl}propyl)phenyl]propanoic acid Step a: tert-Butyl 3-{3-{3-[2-(benzyloxy)phenyl]propyl}-5-[2-(1,3-dioxo-1,3-dihydro-2H-isoindol-2-yl)ethyl]phenyl}propanoate The experimental procedure is identical to that of Example 1, Step a, using the compound of Preparation C, Step e, as starting material instead of the compound of Preparation A, Step e.

Step b: tert-Butyl 3-{3-[2-(1,3-dioxo-1,3-dihydro-2H-isoindol-2-yl)ethyl]-5-[3-(2-hydroxyphenyl)propyl]phenyl}propanoate 10% palladium hydroxide is added to 8.40 mmol of the compound obtained in the above Step dissolved in 80 ml of ethanol. The mixture is hydrogenated for 2½ hours and the solvent is evaporated off.

Step c: tert-Butyl 3-{3-(3-{2-[3-(dimethylamino)propoxy]phenyl}propyl)-5-[2-(1,3-dioxo-1,3-dihydro-2H-isoindol-2-yl)ethyl]phenyl}propanoate The experimental procedure is identical to that of Example 2, Step b, using the compound prepared in the above Step as starting material.

Step d: tert-Butyl 3-[3-(2-aminoethyl)-5-(3-{2-[3-(dimethylamino)propoxy]-phenyl}propyl)phenyl]propanoate The experimental procedure is identical to that of Example 1, Step c, using the compound prepared in the above Step as starting material.

Step e: 3-[3-(2-{[(4-Chlorophenyl)sulphonyl]amino}ethyl)-5-(3-{2-[3-(dimethylamino)propoxy]phenyl}propyl)phenyl]propanoic acid Deprotection of the amine, addition of benzenesulphonyl chloride and finally hydrolysis of the ester are identical to the experimental methods used in Example 1, Step c, Step d and finally Step e, respectively.

Elemental microanalysis:

|  | C | H | Cl | N | S |
|---|---|---|---|---|---|
| % calculated | 63.41 | 6.69 | 6.04 | 4.77 | 5.46 |
| % found | 62.93 | 6.69 | 6.60 | 4.70 | 5.35 |

PHARMACOLOGICAL STUDY

Example A

Platelet Aggregation in Man

Venous blood is obtained from human volunteers who have not taken aspirin for at least 14 days prior to the experiment. The blood is removed over sodium citrate (0.109 M) (1 vol. of citrate over 9 vol. of blood). Platelet-rich plasma (PRP) is obtained by centrifugation (20° C.) at 200 g for 10 minutes. The number of platelets is on average 250000 PL/mm$^3$. The PRP is stored at room temperature until the test and is used within 2 hours of having been taken. The TXA$_2$ agonist U46619 is used at a concentration of 1 $\mu$M and 5-hydroxytryptamine is used at a concentration of 10 $\mu$M, the latter in the presence of 0.3 $\mu$M adenosine diphosphate and 1 $\mu$M adrenalin.

The compounds of the invention inhibit platelet aggregation induced by the TXA$_2$ agonist as well as that produced by 5-hydroxytryptamine. By way of example, the IC$_{50}$ values of the compound of Example 2 in the two experiments are 3.3 $\mu$M and 0.96 $\mu$M respectively.

The values indicate that the compounds of the invention are powerful platelet anti-aggregants, which act in a balanced manner on the two activation routes, that of TXA$_2$ and that of serotonin.

Example B

Pharmaceutical Composition

Formulation for the preparation of 1000 tablets each containing a dose of 5 mg:

| compound of Example 4 | 5 g |
|---|---|
| hydroxypropyl methylcellulose | 2 g |
| wheat starch | 10 g |
| lactose | 100 g |
| magnesium stearate | 3 g |

We claim:
1. A compound of formula (I):

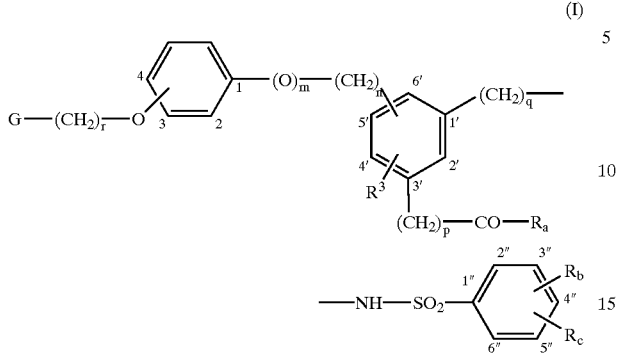

wherein:
G represents a group:

wherein $R^1$ and $R^2$ independently represent a hydrogen atom, or an alkyl, cycloalkyl, optionally substituted aryl, optionally substituted arylalkyl, cycloalkyl, cycloalkylalkyl, optionally substituted heteroaryl or optionally substituted heteroarylalkyl group, or
$R^1$ and $R^2$ together with the nitrogen atom form a heterocycloalkyl group of formula

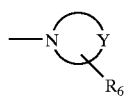

having from 5 to 7 ring members, wherein Y represents a nitrogen atom, an oxygen atom or a $CH_2$ group and $R_6$ represents a hydrogen atom or an alkyl, cycloalkyl, cycloalkylalkyl, optionally substituted aryl, optionally substituted arylalkyl, optionally substituted arylcarbonyl, optionally substituted arylcarbonylalkyl, optionally substituted diarylalkyl, optionally substituted diarylalkenyl, optionally substituted heteroaryl, optionally substituted heteroarylalkyl, optionally substituted heteroarylcarbonyl or optionally substituted heteroarylcarbonylalkyl group,
$R^3$ represents a hydrogen atom or an alkyl or optionally substituted phenyl group,
$R_a$ represents a hydroxy, alkoxy, optionally substituted aryloxy, optionally substituted arylalkyloxy, amino, alkylamino, dialkylamino, optionally substituted arylamino or optionally substituted arylalkylamino group,
$R_b$ and $R_c$, which may be identical or different, each represents a hydrogen atom, a halogen atom, an alkyl group, an alkoxy group, a hydroxy group or a trihaloalkyl group,
m is an integer of from 0 to 1 inclusive,
n and q are identical or different integers of from 0 to 6 inclusive,
p and r are identical or different integers of from 1 to 6 inclusive, its enantiomers, diastereoisomers, or an addition salt thereof with a pharmaceutically acceptable acid or base, wherein:
the term "alkyl" denotes a linear or branched chain having from 1 to 6 carbon atoms,
the term "alkoxy" denotes a linear or branched alkyl-oxy group having from 1 to 6 carbon atoms,
the term "trihaloalkyl" denotes a carbon chain having from 1 to 3 carbon atoms and from 1 to 3 identical or different halogen atoms,
the term "alkenyl" denotes a chain having from 2 to 6 carbon atoms and containing from 1 to 3 double bonds,
the term "cycloalkyl" denotes a saturated cyclic group having from 3 to 8 carbon atoms,
the term "aryl" denotes a phenyl or naphthyl group,
the term "heteroaryl" denotes an aromatic monocyclic group, or a bicyclic group in which at least one of the rings is aromatic, having from 5 to 11 ring members and from 1 to 5 hetero atoms selected from nitrogen, oxygen and sulphur,
the terms "diarylalkyl" and "diarylalkenyl" denote, respectively, alkyl and alkenyl groups as defined hereinbefore, substituted by two identical or different aryl groups as defined hereinbefore,
the term "substituted" relating to phenyl, aryl, arylalkyl, arylcarbonyl, arylcarbonylalkyl, diarylalkyl, diarylalkenyl, heteroaryl, heteroarylalkyl, heteroarylcarbonyl, heteroarylcarbonylalkyl, arylamino and arylalkylamino denotes that the groups are substituted in the aromatic moiety by one or two identical or different substituents selected from halogen atoms and alkyl groups, alkoxy groups, hydroxy groups, cyano groups, nitro groups, amino groups (optionally substituted by one or two alkyl groups) and groups $C(O)R_d$, $R_d$ representing a group selected from hydroxy, alkoxy and amino, wherein the heteroaryl and heteroarylalkyl groups may also be substituted by an oxo group on the non-aromatic moiety of the heteroaryl.

2. A compound of claim 1, wherein p is 2.
3. A compound of claim 1, wherein q is 2.
4. A compound of claim 1, wherein $R^3$ represents a hydrogen atom.
5. A compound of claim 1, wherein $R_a$ represents a hydroxy group.
6. A compound of claim 1, wherein $R_b$ represents a halogen atom.
7. A compound of claim 1, wherein $R_c$ represents a hydrogen atom.
8. A compound of claim 1, wherein p and q are each 2, $R_a$ represents a hydroxy group, $R^3$ and $R_c$ each represent a hydrogen atom, $R_b$ represents a halogen atom and G represents amino, dialkylamino or arylalkylamino group or a heterocycloalkyl group of formula

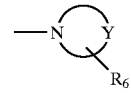

wherein Y represents a nitrogen atom, an oxygen atom or a $CH_2$ group and $R_6$ is selected from a hydrogen atom and the groups optionally substituted aryl and optionally substituted heteroaryl.

9. A compound of claim 1, wherein G represents a dialkylamino group.
10. A compound of claim 1, wherein G represents a substituted heterocycloalkyl group

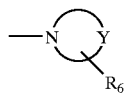

wherein:

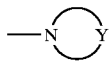

represents a group having 5 or 6 ring members, such as pyrrolyl, morpholino, piperidyl or piperazinyl, and $R_6$ attached to a carbon or nitrogen atom of the heterocycloalkyl represents a hydrogen atom, a phenyl substituent optionally substituted by a halogen atom, or a heteroaryl group having 9 ring members that contains one or two hetero atoms selected from nitrogen, oxygen and sulphur, and which group may optionally be substituted by a halogen atom.

11. A compound of claim 1, wherein the optionally substituted heteroaryl group represents a benzisoxazolyl group optionally substituted by a halogen atom, or a benzisothiazolyl group optionally substituted by a halogen atom.

12. A compound of claim 1, wherein the substituent G—(CH$_2$)$_r$—O— is attached to one of the two carbon atoms in positions 2 or 4 of the phenyl group.

13. A compound of claim 1, wherein the substituent

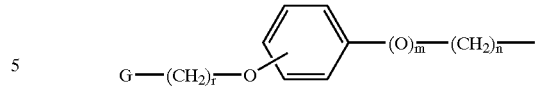

is attached to the 5' carbon atom of the phenyl group.

14. A compound of claim 1, wherein $R_b$ is attached to the 4" carbon atom of the phenyl group.

15. A compound of claim 1, which is 3-[3-(2-{[(4-chlorophenyl)sulphonyl]amino}ethyl)-5-(2-{2-[3-(dimethylamino)propoxy]-phenyl}ethyl)phenyl]propanoic acid.

16. A compound of claim 1, which is 3-[3-(2-{[(4-chlorophenyl)sulphonyl]amino}ethyl)-5-(2-{2-[2-(1-pyrrolidinyl)ethoxy]phenyl}ethyl)phenyl]propanoic acid.

17. A compound of claim 1, which is 3-[3-(2-{[(4-chlorophenyl)sulphonyl]amino}ethyl)-5-(2-{2-[2-(4-morpholinyl)ethoxy]phenyl}ethyl)phenyl]propanoic acid.

18. A pharmaceutical composition useful as a TXA$_2$ receptor antagonist and a 5-HT$_2$ receptor antagonist, comprising as active principle an effective amount of a compound as claimed in claim 1, together with one or more pharmaceutically acceptable excipients or vehicles.

19. A method for treating an animal or human living body afflicted with an atherothrombotic cardiovascular condition comprising the step of administering to the living body an amount of a TXA$_2$ receptor antagonist and a 5-HT$_2$ receptor antagonist compound of claim 1 which is effective for alleviation of the condition.

* * * * *

UNITED STATES PATENT AND TRADEMARK OFFICE
CERTIFICATE OF CORRECTION

PATENT NO. : 6,541,471 B1
DATED : April 1, 2003
INVENTOR(S) : Gilbert Lavielle et al.

It is certified that error appears in the above-identified patent and that said Letters Patent is hereby corrected as shown below:

Title page,
Item [57], ABSTRACT,
Formula (I);

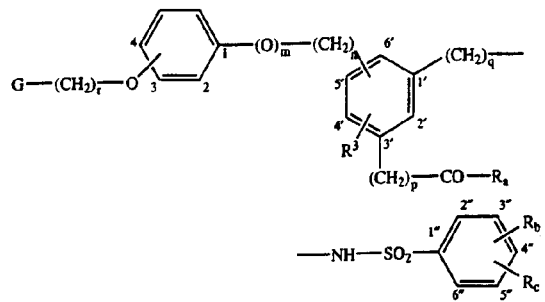

should be

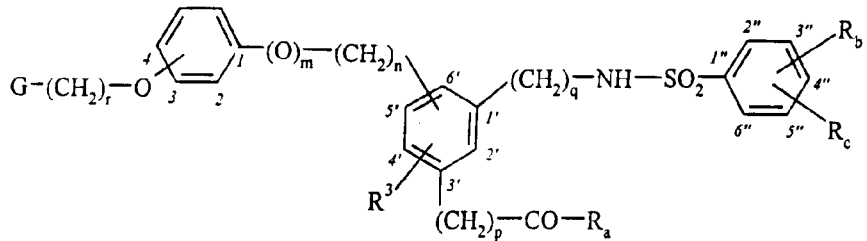

UNITED STATES PATENT AND TRADEMARK OFFICE
CERTIFICATE OF CORRECTION

PATENT NO. : 6,541,471 B1
DATED : April 1, 2003
INVENTOR(S) : Gilbert Lavielle et al.

It is certified that error appears in the above-identified patent and that said Letters Patent is hereby corrected as shown below:

Column 27,
Formula (I);

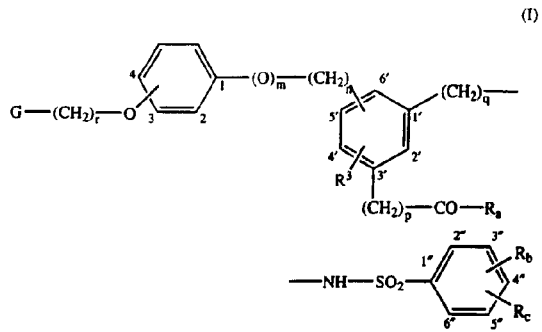

should be

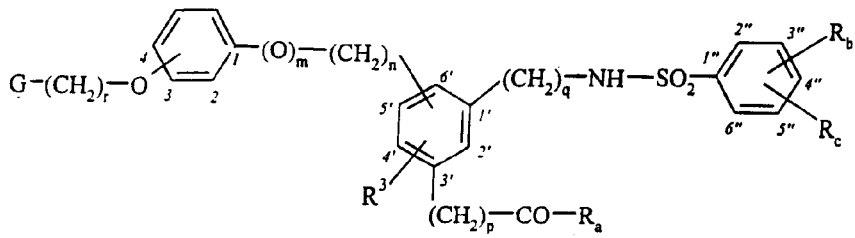

Signed and Sealed this

Fifth Day of August, 2003

JAMES E. ROGAN
*Director of the United States Patent and Trademark Office*